United States Patent
Ketelson et al.

(10) Patent No.: US 10,624,848 B2
(45) Date of Patent: *Apr. 21, 2020

(54) OPHTHALMIC EMULSION

(71) Applicant: ALCON INC., Fribourg (CH)

(72) Inventors: Howard Allen Ketelson, Dallas, TX (US); David L. Meadows, Colleyville, TX (US)

(73) Assignee: Alcon Inc., Fribourg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/405,180

(22) Filed: May 7, 2019

(65) Prior Publication Data

US 2019/0254971 A1     Aug. 22, 2019

Related U.S. Application Data

(63) Continuation of application No. 15/989,383, filed on May 25, 2018, now Pat. No. 10,328,025, which is a continuation of application No. 15/228,589, filed on Aug. 4, 2016, now Pat. No. 10,004,685, which is a continuation of application No. 12/958,763, filed on Dec. 2, 2010, now abandoned.

(60) Provisional application No. 61/266,207, filed on Dec. 3, 2009.

(51) Int. Cl.
| | |
|---|---|
| A61K 9/107 | (2006.01) |
| B01F 17/00 | (2006.01) |
| A61K 9/00 | (2006.01) |

(52) U.S. Cl.
CPC ............ *A61K 9/107* (2013.01); *A61K 9/0048* (2013.01); *B01F 17/0028* (2013.01); *B01F 17/0064* (2013.01); *B01F 17/0085* (2013.01)

(58) Field of Classification Search
CPC ... A61K 9/0048; A61K 9/107; B01F 17/0028; B01F 17/0064; B01F 17/0085
See application file for complete search history.

(56) References Cited

U.S. PATENT DOCUMENTS

| | | |
|---|---|---|
| 3,931,319 A | 1/1976 | Green et al. |
| 4,027,020 A | 5/1977 | Green et al. |
| 4,407,791 A | 10/1983 | Stark |
| 4,525,346 A | 6/1985 | Stark |
| 4,836,986 A | 6/1989 | Ogunbiyi et al. |
| 4,914,088 A | 4/1990 | Glonek et al. |
| 5,037,647 A | 8/1991 | Chowhan et al. |
| 5,278,151 A | 1/1994 | Korb et al. |
| 5,294,607 A | 3/1994 | Glonek et al. |
| 5,300,287 A | 4/1994 | Park |
| 5,371,108 A | 12/1994 | Korb et al. |
| 5,578,586 A * | 11/1996 | Glonek ............... A61K 9/0048  514/558 |
| 5,827,835 A | 10/1998 | Kabra |
| 5,908,866 A * | 6/1999 | Hahnenberger ..... A61K 31/221  514/642 |
| 6,337,092 B1 * | 1/2002 | Khan ................ A61K 9/145  424/489 |
| 6,503,497 B2 | 1/2003 | Chowhan et al. |
| 2002/0035182 A1* | 3/2002 | L'Alloret ............ A61K 8/062  524/315 |
| 2003/0165200 A1 | 9/2003 | Pugel |
| 2003/0180367 A1 | 9/2003 | Parikh et al. |
| 2003/0215470 A1 | 11/2003 | Wilmott et al. |
| 2005/0080043 A1* | 4/2005 | Shahinian, Jr. ....... A61K 9/0043  514/57 |
| 2005/0175697 A1* | 8/2005 | Edgren ............... A61K 9/0004  424/470 |
| 2005/0181041 A1* | 8/2005 | Goldman ............ A61K 9/145  424/456 |
| 2005/0196370 A1* | 9/2005 | Yu ..................... A61K 9/0048  424/70.13 |
| 2008/0025941 A1* | 1/2008 | Rabinovich-Guilatt ................. A61K 8/06  424/70.28 |
| 2009/0068255 A1 | 3/2009 | Yu et al. |
| 2009/0270345 A1 | 10/2009 | Ketelson et al. |

FOREIGN PATENT DOCUMENTS

| | | |
|---|---|---|
| GB | 1593954 A | 7/1981 |
| WO | 91/09523 A1 | 7/1991 |
| WO | 99/06023 A1 | 2/1999 |
| WO | 99/06070 A1 | 2/1999 |

OTHER PUBLICATIONS

Croda, "Myri S40", retrieved on Jun. 22, 2015 from http://www.crodacropcare.com/home.aspx?d=content&view=dtl&s=143&r=256&p=1932&prodID=230.

Aldrich, "Span 65", retrieved on Jun. 22, 2015 from http://www.sigmaaldrich.com/catalog/product/sigma/s2028?ang=en&region=US.

Philipp Erni et al., "Sorbitan Tristerarate Layers at the Air/Water Interface Studied by Shear and Dilatational Interfacial Rheology", Langmuir, 2005, 21, pp. 10555-10563.

Nissim Garti and Dov Reichman, "Surface properties and emulsification activity of galactomannans", Food Hydrocolloids, vol. 8, No. 2, 1994, pp. 155-173.

Donald R. Korb et al., "The effects of anionic and zwitterionic phospholipids on the tear film lipid layer", Adv. Exp. Med. Biol., 2002, 506, pp. 495-499.

Lehninger, "Lipids, Lipoproteins, and Membranes", Biochemistry, 2nd Edition, 1975, Worth Publishers, New York, pp. 279-306.

Leena Peltonen et al., "The Behavior of Sorbitan Surfactants at the Water-Oil Interface: Straight-Chained Hydrocarbons from Pentane to Dodecane as an Oil Phase", Journal of Colloid Interface Science, 240, 2001, pp. 272-276.

* cited by examiner

*Primary Examiner* — Jianfeng Song
(74) *Attorney, Agent, or Firm* — Sheng-Hsin Hu

(57) ABSTRACT

The present invention is directed to an ophthalmic emulsion. The emulsion has a unique combination of ingredients that promotes the stability of small oil droplets within the emulsion. The emulsion also includes a mucoadhesive polymer that aid in delivering a lipid to the ocular surface.

12 Claims, No Drawings

OPHTHALMIC EMULSION

This application is a continuation of U.S. patent application Ser. No. 15/989,383 filed May 25, 2018, which is a continuation of U.S. patent application Ser. No. 15/228,589 filed Aug. 4, 2016, now U.S. Pat. No. 10,004,685; which is a continuation of U.S. patent application Ser. No. 12/958,763 filed Dec. 2, 2010, now abandoned; which application claimed priority to provisional application Ser. No. 61/266,207, filed Dec. 3, 2009.

TECHNICAL FIELD OF THE INVENTION

The present invention is directed to an ophthalmic emulsion. More particularly, the present invention is directed to an ophthalmic emulsion having a unique combination of ingredients that promotes the stability of small oil droplets within the emulsion and promotes the therapeutic delivery capability of the emulsion.

BACKGROUND OF THE INVENTION

There are a variety of types of ophthalmic compositions such as aqueous solutions, aqueous suspensions and others. Ophthalmic compositions are occasionally formulated as emulsions. Ophthalmic emulsions are typically employed in circumstances where it is desirable to include two or more ingredients that are immiscible relative to each other in a single composition and therefore form two separate phases within the composition. Such emulsions can allow a single composition to provide the advantages attributable to both phases (e.g., advantageous delivery characteristics). For example, an emulsion can be formed of oil droplets in an aqueous phase where the oil droplets can be used as carriers for actives such as therapeutic agents (e.g., drugs) or excipients which have poor solubility and/or stability in water.

Examples of emulsions are included in U.S. Pat. Nos. 4,914,088; 5,278,151; 5,294,607; 5,371,108; and 5,578,586. Each of these patents is incorporated herein by reference for all purposes.

It is typically quite desirable for one phase of an emulsion to be substantially uniformly dispersed within the other phase. Such dispersion can significantly effect the capabilities of emulsion to deliver therapeutic ingredients. Moreover, such dispersion is often an indication of the stability of the emulsion itself.

The separate phases of an emulsion can be extremely difficult to evenly disperse throughout a composition since each phase tends to associate with itself rather than the other phase. Thus, the maintenance of the distribution of one phase (i.e., the dispersed phase) within the other phase (i.e., the continuous phase) can be very delicate. Moreover, it is also often difficult to include additional ingredients within an emulsion since many ingredients can act to inhibit the dispersion and/or even distribution of the dispersed phase throughout the continuous phase.

The emulsions of the present invention are two phase systems comprising of oil droplets dispersed in water. The size of the droplets is typically less than 1000 nm but typically greater than 10 nm. Accomplishing such droplet size is difficult since emulsions are typically thermodynamically or otherwise unstable and require one or more excipients to impart stability to the emulsion and prevent the oil droplets from coalescing. De-emulsification of the emulsions needs to be kinetically hindered particularly under exacerbated conditions such as storage of the emulsion at high ambient temperatures (e.g., warehouses during summer months, especially in tropical or central continental or Mediterranean climates, or by a temperature cycle in which the formulations are subjected to cyclical heating and cooling). Additionally, the presence of high ionic strengths in the aqueous phase can lead to de-emulsification.

While small droplet size is difficult to maintain for a simple emulsion, droplet size maintenance can be substantially more complicated when additional ingredients are included in the emulsion (see *Surface properties and emulsification activity of galactomannans*, Food Hydrocolloids, Volume 8, Issue 2, May 1994, Pages 155-173 Nissim Garti, Dov Reichman). For ophthalmic emulsions, it can be particularly difficult to integrate mucoadhesive materials, particularly mucoadhesive polymers, into the emulsion without causing undesirable instability in emulsion oil droplet size. It would be desirable to provide an emulsion that can maintain small droplets and it would be particularly desirable to be able to maintain small droplets in the presence of a mucoadhesive polymer.

Accordingly, there is a need for a method that is capable of producing stable emulsions containing a mucoadhesive polymer. Additionally or alternatively, there remains an outstanding desire for aqueous emulsions which have shear thinning properties to be effective for lubricating and protecting the cornea (dry eye patients). Alternatively or additionally, there remains a need for a method or an alternative method to produce an emulsion comprising a fine dispersion of oil droplets that is preserved with an antimicrobial compound, and particularly a process to produce a stable preserved emulsion.

OBJECTS OF THE INVENTION

It is an object of at least one aspect of the present invention to provide a process that is capable producing a stable emulsion having a small mean droplet in the presence of a mucoadhesive polymer.

It is an object of at least one aspect of the present invention to provide an emulsion which is resistant to phase separation, and particularly offering resistance to phase separation during storage at above standard temperatures and heating/cooling cycling conditions.

SUMMARY OF THE INVENTION

The present invention is directed to an ophthalmic emulsion that includes the following: water forming an aqueous phase; oil forming an oil phase; a hydrophilic surfactant; a hydrophobic surfactant; a charged phospholipid; borate; and a mucoadhesive polymer (e.g., a galactomannan polymer). The oil phase is in droplets within the aqueous phase and the droplets have an average or mean diameter no greater than about 1500 nanometers (nm), more typically no greater than about 1000 nm and still more typically no greater than about 500 nm. These droplets also typically have an average or mean diameter of at least 2 nm, more typically at least 10 nm and still more typically at least 100 nm. The borate and galactomannan polymer cooperatively act to form a gel upon instillation of the emulsion in an eye of an individual.

DETAILED DESCRIPTION OF THE INVENTION

The present invention is predicated upon the provision of an ophthalmic oil in water emulsion wherein the emulsion has average oil droplet size that is relatively small. The emulsion will typically be aqueous and include a substantial amount of water. The emulsion will also typically include an anionic phospholipid, a hydrophilic surfactant (high HLB) and a hydrophobic (low HLB) surfactant. Further, the emulsion will typically include one or more mucoadhesive ingredients (e.g., galactomannan polymers) to aid in maintaining the emulsion on the corneal surface of the eye and/or aid in delivering one or more lipophilic compounds to the corneal surface. The emulsions of the present invention are most desirably used for dry eye therapeutics. However, without limitation, it is also contemplated that the emulsions may be used for drug delivery, vitamin delivery, botanical delivery, contact lens wetting and contact lens lubrication.

Unless otherwise specifically stated all emulsion ingredient amounts or percentages are weight volume percentages (w/v %).

The oil of the emulsion is dispersed throughout the continuous water or aqueous phase as small droplets that are substantially distinct and separate. It should be understood that, as used herein, the phase distinct and separate means that, at any give point in time, the droplets are distinct and separate. However, the droplets of the emulsion can combine and separate over time to maintain an average droplet size or diameter. The droplets of the emulsion of the present invention typically have an average or mean diameter no greater than about 1500 nanometers (nm), more typically no greater than about 1000 nm and still more typically no greater than about 600 nm. These droplets also typically have an average or mean diameter that is typically at least 2 nm, more typically at least 10 nm and still more typically at least 100 nm.

Particle or droplet size analyzers may be used to determine emulsion oil droplet size. For example, a Microtrac S3500 Particle Size Analyzer (Software Version 10.3.1) is a tri-laser particle size analyzer that can be used to measure emulsion oil droplet size. That particular analyzer measures laser light diffracted (scattered) from particles (e.g., droplets) in a flowing stream. The intensity and direction of the scattered light is measured by two optical detectors. Mathematical analysis of the diffraction pattern by the software generates a volume distribution of droplet size. The droplet diameter corresponding to 90% of the cumulative undersize distribution by volume is used.

The emulsion of the present invention is an oil in water emulsion. The oil can be any of numerous mineral, vegetable, and synthetic substances and/or animal and vegetable fats or any combination of oils. The oil can be soluble in various organic solvents such as ether but not in water. The oil phase can comprise, if desired a liquid hydrocarbon, such as a mineral oil, paraffin oils, petrolatum or hydrocarbon oils. Mineral oil is particularly preferred. A silicone oil may also be used. The oil phase can additionally include a waxy hydrocarbon, such as paraffin waxes, hydrogenated castor oil, Synchrowax HRC, Carnabau, beeswax, modified beeswaxes, microcrystalline waxes, and polyethylene waxes. The oil is typically at least 0.01 w/v %, more typically at least 0.1 w/v % and even more typically 0.8 w/v % of the emulsion. The oil is also typically no greater than about 20 w/v %, more typically no greater than about 5 w/v % and even more typically no greater than about 3 or even 1.5 w/v % of the emulsion The emulsion of the present invention also typically incorporates two or more surfactants, which act as emulsifiers aiding in the emulsification of the emulsion. Typically, these surfactants are non-ionic. The concentration of emulsifying surfactant in the emulsion is often selected in the range of from 0.1 to 10% w/v, and in many instances from 0.5 to 5% w/v. It is preferred to select at least one emulsifier/ surfactant which is hydrophilic and has an HLB value of at least 8 and often at least 10 (e.g., 10 to 18). It is further preferred to select at least one emulsifier/surfactant which is hydrophobic and has an HLB value of below 8 and particularly from 1 to 6. By employing the two surfactants/emulsifiers together in appropriate ratios, it is readily feasible to attain a weighted average HLB value that promotes the formation of an emulsion. For most emulsions according to the present invention, the average HLB value is chosen in the range of about 6 to 12, and for many from 7 to 11.

For example:

For example, the HLB values for exemplary surfactants and mineral oil are as follows: hydrophobic surfactant (2.1), hydrophilic surfactant (16.9) and mineral oil (10.5). The concentrations of hydrophobic surfactant and hydrophilic surfactant used in exemplary emulsions were 0.38% and 0.29% based on these calculations.

$$.29/.67 = 0.43 \text{ and } .38/.67 = 0.57$$

$$\text{hydrophobic surfactant} \quad 2.1 \times 0.43 = 0.90$$
$$\text{hydrophilic surfactant} \quad 16.9 \times 0.57 = \underline{9.63}$$
$$10.53$$

The ratio between hydrophobic surfactant and hydrophilic surfactant is equal to 1.32 which can be used to select the proper ratio of concentrations to be used for the two surfactants. The concentrations of hydrophobic surfactant and hydrophilic surfactant used in exemplary emulsions were 0.38% and 0.29% based on these calculations.

The hydrophilic surfactant is typically present in the emulsion in an amount that is at least about 0.01 w/v %, more typically at least about 0.08 w/v % and even more typically at least about 0.14 w/v %. The hydrophilic surfactant is typically present in the emulsion in an amount that is no greater than about 1.5 w/v %, more typically no greater than about 0.8 w/v % and even more typically no greater than about 0.44 w/v %.

The hydrophilic surfactant can be a fatty acid, an ester, an ether, an acid or any combination thereof. The hydrophilic surfactant may be ionic or non-ionic, but is preferably non-ionic. Many suitable surfactants/emulsifiers are non-ionic ester or ether emulsifiers comprising a polyoxyalkylene moiety, especially a polyoxyethylene moiety, often containing from about 2 to 80, and especially 5 to 60 oxyethylene units, and/or contain a polyhydroxy compound such as glycerol or sorbitol or other alditols as hydrophilic moiety. The hydrophilic moiety can contain polyoxypropylene. The emulsifiers additionally contain a hydrophobic alkyl, alkenyl or aralkyl moiety, normally containing from about 8 to 50 carbons and particularly from 10 to 30 carbons. Examples of hydrophilic surfactants/emulsifiers include ceteareth-10 to-25, ceteth-10-25, steareth-10-25, and PEG-15-25 stearate or distearate. Other suitable examples include C10-C20 fatty acid mono, di or tri-glycerides. Further examples include C18-C22 fatty alcohol ethers of polyethylene oxides (8 to 12 EO). One particularly preferred hydrophilic surfactant is polyoxyethylene-40-stearate, which is sold under the tradename MYRJ-52, which is commercially available from Nikko Chemicals.

The hydrophobic surfactant is typically present in the emulsion in an amount that is at least about 0.01 w/v %, more typically at least about 0.11 w/v % and even more typically at least about 0.16 w/v %. The hydrophobic surfactant is typically present in the emulsion in an amount that is no greater than about 10.0 w/v %, more typically no greater than about 2.0 w/v % and even more typically no greater than about 0.62 w/v %.

The hydrophobic surfactant can be a fatty acid, an ester, an ether, an acid or any combination thereof. The hydrophobic surfactant may be ionic or non-ionic, but is preferably non-ionic. The hydrophobic surfactant will typically include a hydrophobic moiety. The hydrophobic moiety can be either linear or branched and is often saturated, though it can be unsaturated, and is optionally fluorinated. The hydrophobic moiety can comprise a mixture of chain lengths, for example those deriving from tallow, lard, palm oil sunflower seed oil or soya bean oil. Such non-ionic surfactants can also be derived from a polyhydroxy compound such as glycerol or sorbitol or other alditols. Examples of hydrophobic surfactants include, without limitation, sorbitan fatty acid esters such as sorbitan monoleate, sorbitan monostearate, sorbitan monolaurate, sorbitan monopalmitate, sorbitan monoisostearate, sorbitan trioleate, sorbitan tristearate, sorbitan sesquioleate, sorbitan sesquistearate, combinations thereof or the like. One particularly preferred hydrophobic surfactant is a sorbitan tristearate sold under the tradename SPAN-65, which is commercially available from Croda Worldwide.

The types of galactomannans that may be used in the present invention are typically derived from guar gum, locust bean gum and tara gum. As used herein, the term "galactomannan" refers to polysaccharides derived from the above natural gums or similar natural or synthetic gums containing mannose or galactose moieties, or both groups, as the main structural components. Preferred galactomannans of the present invention are made up of linear chains of (1-4)-.beta.-D-mannopyranosyl units with .alpha.-D-galactopyranosyl units attached by (1-6) linkages. With the preferred galactomannans, the ratio of D-galactose to D-mannose varies, but generally will be from about 1:2 to 1:4. Galactomannans having a D-galactose:D-mannose ratio of about 1:2 are most preferred. Additionally, other chemically modified variations of the polysaccharides are also included in the "galactomannan" definition. For example, hydroxyethyl, hydroxypropyl and carboxymethylhydroxypropyl substitutions may be made to the galactomannans of the present invention. Non-ionic variations to the galactomannans, such as those containing alkoxy and alkyl (C1-C6) groups are particularly preferred when a soft gel is desired (e.g., hydroxylpropyl substitutions). Substitutions in the non-cis hydroxyl positions are most preferred. An example of non-ionic substitution of a galactomannan of the present invention is hydroxypropyl guar, with a molar substitution of about 0.4. Anionic substitutions may also be made to the galactomannans. Anionic substitution is particularly preferred when strongly responsive gels are desired. A galactomannan is typically present in a formulation of the present invention at a concentration of at least about 0.005 w/v %, more typically at least about 0.01 w/v % and even more typically at least about 0.03 w/v %, but typically no greater than about 5 w/v %, more typically no greater than about 1.0 w/v %, still more typically no greater than about 0.3 w/v % and even still more typically no greater than about 0.08 w/v %. Preferred galactomannans of the present invention are guar and hydroxypropyl guar.

The emulsion may include additional or alternative polymeric ingredients and/or viscosity agents. Examples include, without limitation, carboxymethylcellulose, hydroxypropylmethyl cellulose, hydroxyethyl cellulose, carboxyvinyl polymer, xanthan gum, hyaluronic acid, any combinations thereof or the like.

The emulsion of the present invention includes at least one phospholipid for aiding in maintaining the stability of the emulsion and for reducing droplet size of the oil. It is known that complex phospholipids can contain a polar group at one end of their molecular structure and a non-polar group at the opposite end of their molecular structure. A discussion of phospholipids can be found in Lehninger, Biochemistry, 2 ed., Worth Publishers, New York, pp. 279-306, incorporated herein by reference for all purposes.

Many complex phospholipids are known to the art. They differ in size, shape and the electric charge of their polar head groups. Phosphoglycerides are compounds where one primary hydroxyl group of glycerol is esterified to phosphoric acid, and the other two hydroxyl groups are esterified with fatty acids. The parent compound of the series is, therefore, the phosphoric acid ester of glycerol. This compound has an asymmetric carbon atom and, therefore, the term phosphoglycerides includes stereoisomers. All phosphoglycerides have a negative charge at the phosphate group at pH 7, and the $pK_a$ of this group is in the range of 1 to 2. The head groups of phosphatidylinositol, phosphatidylglycerol including diphosphatidylglycerols (having the common name cardiolipins) and the phosphatidylsugars have no electric charge, and all are polar because of their high hydroxyl group content. Because of the negative charge of the phosphate group and the absence of a charge in the head group, the net charge of each of these materials is negative, and these materials are within the scope of the invention. Suitable phospholipids are those carrying a net positive or negative charge under conditions of use. The preferred materials are those carrying a net negative charge because the negatively charged material will be repelled by the negatively charged ocular surface thereby permitting the maintenance of a relatively thick aqueous layer upon application to the eye. The most preferred phospholipid is an anionic phospholipid named dimyristoyl phosphatidylglycerol (DMPG), which is a polyol with a net negative charge. Phosphatidylglycerol or a phosphatidylinositol are other examples. Suitable phospholipid additives are disclosed in the above cited U.S. Pat. No. 4,914,088, which is fully incorporated herein by reference for all purposes.

Most phospholipids are water insoluble. However, for application to the eye, it is desirable that the phospholipid be homogeneously distributed throughout an aqueous medium. For those few phospholipids having a solubility within a useful concentration range for use as a treatment composition, a simple aqueous solution of the phospholipid in saline is satisfactory. For those phospholipids that are essentially water insoluble, an aqueous composition in the form of an emulsion may be used. An emulsion provides a treatment composition where the phase containing the phospholipid component is homogeneously distributed throughout the aqueous vehicle.

The concentration of the phospholipid in the treatment composition may vary within wide limits. A treatment composition containing the complex phospholipid in an amount as low as 0.01 weight percent provides some benefit. When the treatment composition is in the form of an emulsion, compositions containing the phospholipid in elevated concentrations approaching collapse of the emulsion into separate aqueous and phospholipid phases is possible. A clinically practical concentration range for the phospholipid in its vehicle varies from about 0.05 to 7.0 w/v % phospholipid by weight, and more preferably varies from about 0.1 and 5.0 w/v %. It should be noted that the most desired concentration for the phospholipid in the aqueous composition will vary from subject to subject.

Other additives may be present in the phospholipid treatment composition including neutral lipids such as one or more triglycerides, cholesterol esters, the natural waxes and cholesterol; higher molecular weight isoprenoids; stabilizers; preservatives; pH adjustors to provide a composition preferably having a pH between about 6 and 8 and more preferably between about 7.0 and 7.4; salt in sufficient concentration to form an isotonic composition; medicants; etc.

As indicated above, the emulsions of the present invention can include borate or borate/polyol buffer systems. As used herein, the term "borate" includes boric acid, salts of boric acid, other pharmaceutically acceptable borates, and combinations thereof. The following borates are particularly preferred: boric acid, sodium borate, potassium borate, calcium borate, magnesium borate, manganese borate, and other such borate salts.

As used herein, the term "polyol" includes any compound having at least one hydroxyl group on each of two adjacent carbon atoms that are not in trans configuration relative to each other. The polyols can be linear or cyclic, substituted or unsubstituted, or mixtures thereof, so long as the resultant complex is water soluble and pharmaceutically acceptable. Examples of such compounds include: sugars, sugar alcohols, sugar acids and uronic acids. Preferred polyols are sugars, sugar alcohols and sugar acids, including, but not limited to: mannitol, glycerin, xylitol and sorbitol. Especially preferred polyols are mannitol and sorbitol; most preferred is sorbitol.

The use of borate-polyol complexes in ophthalmic compositions is described in U.S. Pat. No. 6,503,497 (Chowhan); the entire contents of which are hereby incorporated in the present specification by reference. The emulsions of the present invention preferably contain one or more borates in a concentration that is at least about 0.01% w/v, more typically at least about 0.3% w/v and even more typically at least about 0.8% w/v, but typically no greater than about 5.0% w/v, more typically no greater than about 2.0% w/v and even more typically no greater than about 1.2% w/v. It is generally desirable for the amount of the one or more borates to be sufficient to allow the formation of borate/polyol complexes and, when desired, to aid in gelling the galactomannan polymer upon application of the emulsion to the eye.

The compositions of the present invention typically include a preservative. Potential preservatives include, without limitation, hydrogen peroxide, chlorine containing preservatives such as benzalkonium chloride or others. According to a preferred aspect, however, the ophthalmic composition of the present invention is substantially free of any chloride containing preservatives and, particularly, is substantially free of benzalkonium chloride. Most preferred preservatives included in the ophthalmic composition are polymeric quaternary ammonium compounds.

As used herein, the phrase "substantially free of" as it refers to an ingredient of the ophthalmic composition means that it is contemplated that the ophthalmic solution can be either entirely devoid of that particular ingredient or includes only a nominal amount of that particular ingredient.

The polymeric quaternary ammonium compounds useful in the compositions of the present invention are those which have an antimicrobial effect and which are ophthalmically acceptable. Preferred compounds of this type are described in U.S. Pat. Nos. 3,931,319; 4,027,020; 4,407,791; 4,525,346; 4,836,986; 5,037,647 and 5,300,287; and PCT application WO 91/09523 (Dziabo et al.). The most preferred polymeric ammonium compound is polyquaternium 1, otherwise known as POLYQUAD® or ONAMERM® with a number average molecular weight between 2,000 to 30,000. Preferably, the number average molecular weight is between 3,000 to 14,000.

The polymeric quaternary ammonium compounds are generally used in the compositions of the present invention in an amount that is greater than about 0.00001 w/v %, more typically greater than about 0.0003 w/v % and even more typically greater than about 0.0007 w/v % of the ophthalmic composition. Moreover, the polymeric quaternary ammonium compounds are generally used in the compositions of the present invention in an amount that is less than about 3 w/v %, more typically less than about 0.003 w/v % and even more typically less than about 0.0015 w/v % of the ophthalmic composition.

The emulsion of the present invention can include any of a multitude of ophthalmic therapeutic agents. Non-limiting examples of potential ophthalmic therapeutic agents for the present invention include: anti-glaucoma agents, anti-angiogenesis agents; anti-infective agents; anti-inflammatory agents; growth factors; immunosuppressant agents; and anti-allergic agents. Anti-glaucoma agents include beta-blockers, such as betaxolol and levobetaxolol; carbonic anhydrase inhibitors, such as brinzolamide and dorzolamide; prostaglandins, such as travoprost, bimatoprost, and latanoprost; seretonergics; muscarinics; dopaminergic agonists. Anti-angiogenesis agents include anecortave acetate (RETAANE™, Alcon™ Laboratories, Inc. of Fort Worth, Tex.) and receptor tyrosine kinase inhibitors (RTKi). Anti-inflammatory agents include non-steroidal and steroidal anti-inflammatory agents, such as triamcinolone actinide, suprofen, diclofenac, ketorolac, nepafenac, rimexolone, and tetrahydrocortisol. Growth factors include EGF or VEGF. Anti-allergic agents include olopatadine and epinastine. The ophthalmic drug may be present in the form of a pharmaceutically acceptable salt.

The present invention can be particularly useful for delivery therapeutic agents that relieve symptoms of dry eye conditions. Examples include, without limitation, steroidal and/or non-steroidal anti-inflammatory agents; selective PDE IV inhibitors such as cilomilast, cyclosporins, combinations thereof or the like. The emulsion of the invention can also be used in other fields, such as to deliver cooling agents, deliver antioxidants (omega-3 and omega-6 fatty acids) and other bioactives for ophthalmic uses. For example, nutriceuticals such as vitamin A (retinol), vitamin D (calciferol), vitamin E, tocopherols, vitamin K (quinone), beta-carotene (pro-vitamin-A) and combinations thereof.

Generally, amounts of therapeutic agent, when used, can be quite variable depending upon the agent or agents used. As such, the concentration of therapeutic agent can be at least about 0.005 w/v %, more typically at least about 0.01 w/v % and even more typically at least about 0.1 w/v %, but typically no greater than about 10 w/v %, more typically no greater than about 4.0 w/v %, still more typically no greater than about 2.0 w/v %.

The emulsions of the present invention may optionally comprise one or more additional excipients and/or one or more additional active ingredients. Excipients potentially used in the ophthalmic emulsions include, but are not limited to, demulcents, tonicity agents, preservatives, chelating agents, buffering agents, and surfactants. Other excipients comprise solubilizing agents, stabilizing agents, comfort-enhancing agents, polymers, emollients, pH-adjusting agents and/or lubricants.

The emulsion is typically aqueous and therefore includes a substantial amount of water, which is typically purified.

The emulsion typically includes water at a concentration of at least about 50 w/v %, more typically at least about 85 w/v % and even more typically at least about 93 w/v %, but typically no greater than about 99.99 w/v %, more typically no greater than about 99.0 w/v %, still more typically no greater than about 0.3 w/v % and even still more typically no greater than about 98 w/v %.

The emulsion of the present invention may be formed using a variety of combining and mixing protocol and techniques known to those skilled in the art. According to one preferred embodiment, however, the ingredients are mixed and combined according to a specific protocol. In such protocol, multiple admixtures are formed and those admixtures are combined to form the emulsion. The first admixture is formed by mixing the oil and the surfactants at an elevated temperature to form an oil phase admixture. The second admixture is formed mixing the anionic phospholipid into purified water at an elevated temperature to form a water phase admixture. Thereafter, the oil phase admixture and the water phase admixture are mixed at an elevated temperature and subsequently homogenized using a homogenizer to form an initial emulsion. A third admixture is formed by mixing the galactomannan polymer with water and adjusting pH as needed to form a galactomannan polymer slurry. The galactomannan polymer slurry is then mixed with initial emulsion and form a polymer enhanced emulsion. A fourth admixture is formed by mixing any combination of the following to form a salt solution: borate, polyol, preservative and any other ingredients. The salt solution and the enhanced emulsion are then mixed followed by the addition of a sufficient quantity (Q.S.) of water and pH adjustment.

The emulsion can be used as an ocular lubricant, a drug delivery vehicle or the like. However, it has been found particularly desirable for use as a dry eye therapy. As such, a individual diagnosed with or experiencing dry eye symptoms can dispense the emulsion to that individual's eye for alleviating those dry eye symptoms. Typically the emulsion is provided in an eye dropper such that an individual may instill one, two or more drops into one or both of their eyes on a regular or as needed basis. Upon instillation, the emulsion will typically gel upon the corneal surface of the eye allowing for more significant therapeutic effects such as aiding in the delivery of lipids to the ocular surface.

Advantageously, the stability of the oil in water emulsion of the present invention can facilitate lubrication and/or the delivery of lipids (e.g., lipid therapeutic agents) to the ocular surface. These lipids can aid in stabilizing the tear film and/or can provide alternative therapeutic advantages to the eye. Moreover, the mucoadhesive polymer can aid residence time of the emulsions upon the eye such that the emulsions can be more efficacious.

EXAMPLES

TABLE I

| COMPONENT | CONCENTRATION PERCENT, W/V |
|---|---|
| Polyquaternium-1 | 0.001 + 10%* |
| HP-Guar | 0.05 |
| Mineral oil | 1.0 |
| Boric Acid | 1.0 |
| Anionic Phospholipid | 0.005 |
| Polyoxyl 40 Stearate | 0.38 |
| Sorbitan Tristearate | 0.29 |

TABLE I-continued

| COMPONENT | CONCENTRATION PERCENT, W/V |
|---|---|
| Propylene Glycol | 0.6 |
| Sorbitol | 0.7 |
| Edetate Disodium | 0.025 |
| Sodium Hydroxide | Adjust pH to 7.0 |
| Hydrochloric Acid | Adjust pH to 7.0 |
| Purified Water | QS 100 |

Table 1 above is a formulation for one exemplary emulsion in accordance with the present invention. It is understood that the weight/volume percents in table I can be varied by ±10%, ±20%, ±30%, ±90% of those weight/volume percents or more and that those variances can be specifically used to create ranges for the ingredients of the present invention. For example, an ingredient weight/volume percent of 10% with a variance of ±20% means that the ingredient can have a weight/volume percentage range of 8 to 12 w/v %.

TABLE II

| Components | Typical Concentration range for testing |
|---|---|
| Polyquaternium-1 | 0-0.001% |
| Mineral Oil | 1 |
| HP-Guar | 0.05-0.18 |
| polyoxyl-40 stearate | 0.19-0.38 |
| Sorbitan tristearate | 0.15-0.29 |
| Anionic Phospholipid | 0-0.1 |
| Boric Acid | 1.0 |
| Sorbitol | 0.7 |
| Propylene Glycol | 0.6 |
| $ZnCl_2$ | 0-0.0015 |

Table 2 above is a formulation for one exemplary emulsion in accordance with the present invention. It is understood that the weight/volume percents in table I can be varied by ±10%, ±20%, ±30%, ±90% of those weight/volume percents or more and that those variances can be specifically used to create ranges for the ingredients of the present invention. For example, an ingredient weight/volume percent of 10% with a variance of ±20% means that the ingredient can have a weight/volume percentage range of 8 to 12 w/v %.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

We claim:

1. An ophthalmic emulsion, the emulsion comprising:
water forming an aqueous phase;
oil forming an oil phase;
a hydrophilic surfactant having an HLB value of at least 10, wherein the hydrophilic surfactant is polyoxyethylene-40-stearate;
a hydrophobic surfactant having an HLB value of below 8, wherein the hydrophobic surfactant is sorbitan tristearate;
a charged phospholipid;
borate;
a mucoadhesive galactomannan polymer; and
a preservative, wherein the emulsion is free of a benzalkonium chloride,
wherein:
i. the oil phase is in droplets within the aqueous phase and the droplets have an average diameter that is no greater than about 1000 nm, but is at least 10 nm, wherein the average diameter is corresponding to 90% of the cumulative undersize distribution by volume measured using a Microtrac S3500 Particle Size Analyzer (Software Version 10.3.1); and
ii. the borate and galactomannan polymer cooperatively act to form a gel upon instillation of the emulsion in an eye of an individual.

2. The emulsion according to claim 1 wherein the oil is a hydrocarbon selected from mineral oil, paraffin oil and petrolatum.

3. The emulsion according to claim 1 wherein the oil is at least 0.1 w/v % and no greater than 5 w/v %.

4. The emulsion according to claim 1 wherein the hydrophilic surfactant is present in the emulsion in an amount that is at least 0.08 w/v % and is present in the emulsion in an amount that is no greater than 0.8 w/v %.

5. The emulsion according to claim 1 wherein the hydrophobic surfactant is present in the emulsion in an amount that is at least 0.11 w/v % and is present in the emulsion in an amount that is no greater than 2.0 w/v %.

6. The emulsion according to claim 1 wherein the mucoadhesive galactomannan polymer is selected from the group consisting of guar and hydroxypropyl guar.

7. The emulsion according to claim 1 wherein the mucoadhesive galactomannan polymer is present in the emulsion at a concentration of at least 0.01 w/v %, but no greater than 1.0 w/v %.

8. The emulsion according to claim 1 wherein the charged phospholipid is an anionic phospholipid named dimyristoyl phosphatidylglycerol.

9. An emulsion according to claim 1 wherein the phospholipid is present in the emulsion in a concentration from 0.05 to 7.0 percent by weight.

10. The emulsion according to claim 1 further comprising a borate/polyol buffer system.

11. The emulsion according to claim 1, the preservative is a polymeric quaternary ammonium compound.

12. The emulsion according to claim 1 wherein the oil phase is in droplets within the aqueous phase and the droplets have an average diameter that is no greater than 500 nm but is at least 100 nm, wherein the average diameter is corresponding to 90% of the cumulative undersize distribution by volume measured using a Microtrac S3500 Particle Size Analyzer (Software Version 10.3.1).

* * * * *